(12) United States Patent
Kawabata et al.

(10) Patent No.: US 12,207,955 B2
(45) Date of Patent: Jan. 28, 2025

(54) RADIATION DETECTOR (71) Applicant: CANON ELECTRON TUBES & DEVICES CO., LTD., Otawara (JP)

(72) Inventors: Tomoki Kawabata, Yaita (JP); Ryo Mibuka, Yaita (JP)

(73) Assignee: CANON ELECTRON TUBES & DEVICES CO., LTD., Otawara (JP)

( * ) Notice: Subject to any disclaimer, the term of this patent is extended or adjusted under 35 U.S.C. 154(b) by 299 days.

(21) Appl. No.: 17/938,414

(22) Filed: Oct. 6, 2022

(65) Prior Publication Data

US 2023/0035605 A1 Feb. 2, 2023

Related U.S. Application Data

(63) Continuation of application No. PCT/JP2020/042720, filed on Nov. 17, 2020.

(30) Foreign Application Priority Data

Apr. 9, 2020 (JP) ................. 2020-070435

(51) Int. Cl.
*A61B 6/00* (2024.01)
*G01T 1/20* (2006.01)
*G01T 7/00* (2006.01)
*H04N 5/32* (2023.01)

(52) U.S. Cl.
CPC ............... *A61B 6/00* (2013.01); *G01T 1/20* (2013.01); *H04N 5/32* (2013.01); *G01T 7/00* (2013.01)

(58) Field of Classification Search
None
See application file for complete search history.

(56) References Cited

U.S. PATENT DOCUMENTS

| 4,889,991 | A | 12/1989 | Ramsey et al. |
| 2001/0053672 | A1* | 12/2001 | Masaki ................. H01Q 1/48 455/129 |

(Continued)

FOREIGN PATENT DOCUMENTS

| CN | 1964592 | * | 5/2007 |
| CN | 106707324 | A | 5/2017 |

(Continued)

OTHER PUBLICATIONS

International Search Report issued Jan. 26, 2021 in PCT/JP2020/042720 filed Nov. 17, 2020, citing documents 1, 16-22 therein, 3 pages.

*Primary Examiner* — Edwin C Gunberg
(74) *Attorney, Agent, or Firm* — Oblon, McClelland, Maier & Neustadt, L.L.P.

(57) ABSTRACT

A radiation detector according to an embodiment includes a housing, an array substrate that is located inside the housing and includes multiple detecting parts detecting radiation directly or in collaboration with a scintillator, a circuit board that is located inside the housing and electrically connected with the array substrate, and a conductive part located between a ground and a plate-shaped body inside the housing, wherein the ground is film-shaped and is located in the circuit board, and the plate-shaped body is conductive and is located in the housing. The conductive part is conductive and includes a softer material than a material of the ground.

20 Claims, 4 Drawing Sheets

(56) References Cited

U.S. PATENT DOCUMENTS

| | | | | |
|---|---|---|---|---|
| 2005/0041347 A1* | 2/2005 | Khorram | ............... | H04B 15/00 |
| | | | | 361/56 |
| 2016/0146952 A1* | 5/2016 | Kim | ..................... | G01T 1/17 |
| | | | | 250/371 |
| 2017/0261621 A1 | 9/2017 | Nagata et al. | | |
| 2017/0281103 A1* | 10/2017 | Han | ................ | A61B 6/4233 |

FOREIGN PATENT DOCUMENTS

| | | |
|---|---|---|
| EP | 3 199 104 A1 | 8/2017 |
| JP | 2557109 B2 | 11/1996 |
| JP | 2000-28736 A | 1/2000 |
| JP | 2007-27455 A | 2/2007 |
| JP | 2009-300084 A | 12/2009 |
| JP | 2012-103268 A | 5/2012 |
| JP | 2012-239657 A | 12/2012 |
| JP | 2013-7712 A | 1/2013 |
| JP | 2014-6233 A | 1/2014 |
| JP | 2017-161408 A | 9/2017 |
| JP | 2018-500534 A | 1/2018 |
| KR | 10-1835089 B1 | 3/2018 |

\* cited by examiner

ID DETECTOR

CROSS-REFERENCE TO RELATED APPLICATIONS

This application is a continuation application of International Application No. PCT/JP2020/042720, filed on Nov. 17, 2020; and is also based upon and claims the benefit of priority from the Japanese Patent Application No. 2020-070435, filed on Apr. 9, 2020; the entire contents of which are incorporated herein by reference.

FIELD

Embodiments of the invention relate to a radiation detector.

BACKGROUND

An X-ray detector is an example of a radiation detector. For example, a scintillator, an array substrate, and a circuit board are provided in a general X-ray detector. The scintillator converts incident X-rays into fluorescence. The array substrate includes multiple photoelectric conversion parts including photoelectric conversion elements and thin film transistors, and converts the fluorescence generated by the scintillator into a charge. An analog circuit and a digital circuit are provided in the circuit board. The analog circuit reads the charge (an image data signal) from multiple photoelectric conversion parts. The digital circuit configures an X-ray image based on the image data signal that is read.

When the X-ray detector is used in medical care, the X-ray irradiation amount on the human body is kept as low as possible; therefore, the intensity of the X-rays incident on the X-ray detector is extremely weak. Therefore, because the image data signal read from the multiple photoelectric conversion parts is exceedingly faint, there is a risk that the quality of the X-ray image may be degraded when even slight noise is mixed into the image data signal.

Also, in recent years, to perform an accurate diagnosis, it is desirable to realize higher density by providing more photoelectric conversion parts and by faster reading and processing of the image data signal. Therefore, faster processing in a digital circuit is necessary; the operating clock is faster; and the noise is increased. As a result, there is a risk that the quality of the X-ray image may be further reduced because noise is more easily mixed into the analog circuit.

It is therefore desirable to develop a radiation detector in which the noise can be reduced.

DETAILED DESCRIPTION

A radiation detector according to an embodiment includes a housing, an array substrate that is located inside the housing and includes multiple detecting parts detecting radiation directly or in collaboration with a scintillator, a circuit board that is located inside the housing and electrically connected with the array substrate, and a conductive part located between a ground and a plate-shaped body inside the housing, wherein the ground is film-shaped and is located in the circuit board, and the plate-shaped body is conductive and is located in the housing. The conductive part is conductive and includes a softer material than a material of the ground.

Embodiments will now be illustrated with reference to the drawings. Similar components in the drawings are marked with the same reference numerals; and a detailed description is omitted as appropriate.

Radiation detectors according to embodiments of the invention can also be applied to various radiation other than X-rays such as γ-rays, etc. Herein, as an example, the case relating to X-rays is described as a typical example of radiation. Accordingly, applications to other radiation also are possible by replacing "X-ray" of embodiments described below with "other radiation".

Also, an X-ray detector 1 illustrated below can be an X-ray planar sensor that detects an X-ray image that is a radiation image. X-ray planar sensors can be largely divided into direct conversion and indirect conversion.

An indirect conversion X-ray detector includes, for example, an array substrate including multiple photoelectric conversion parts, and a scintillator that is located on the multiple photoelectric conversion parts and converts the X-rays into fluorescence (visible light). In an indirect conversion X-ray detector, X-rays incident from the outside are converted into fluorescence by the scintillator. The generated fluorescence is converted into charge by the multiple photoelectric conversion parts.

A direct conversion X-ray detector includes, for example, a photoelectric conversion film made of amorphous selenium, etc. In the direct conversion X-ray detector, X-rays incident from the outside are absorbed by the photoelectric conversion film and directly converted into charge. Known technology is applicable to the basic configuration of the direct conversion X-ray detector; and a detailed description is therefore omitted.

Although the indirect conversion X-ray detector 1 is illustrated as an example hereinbelow, the invention can also be applied to a direct conversion X-ray detector. In other words, it is sufficient for the X-ray detector to include multiple detecting parts that convert X-rays into electrical information. For example, the detecting part can detect X-rays directly or in collaboration with a scintillator.

Also, for example, the X-ray detector 1 can be used in general medical care, etc. However, the applications of the X-ray detector 1 are not limited to general medical care.

Figure 1:
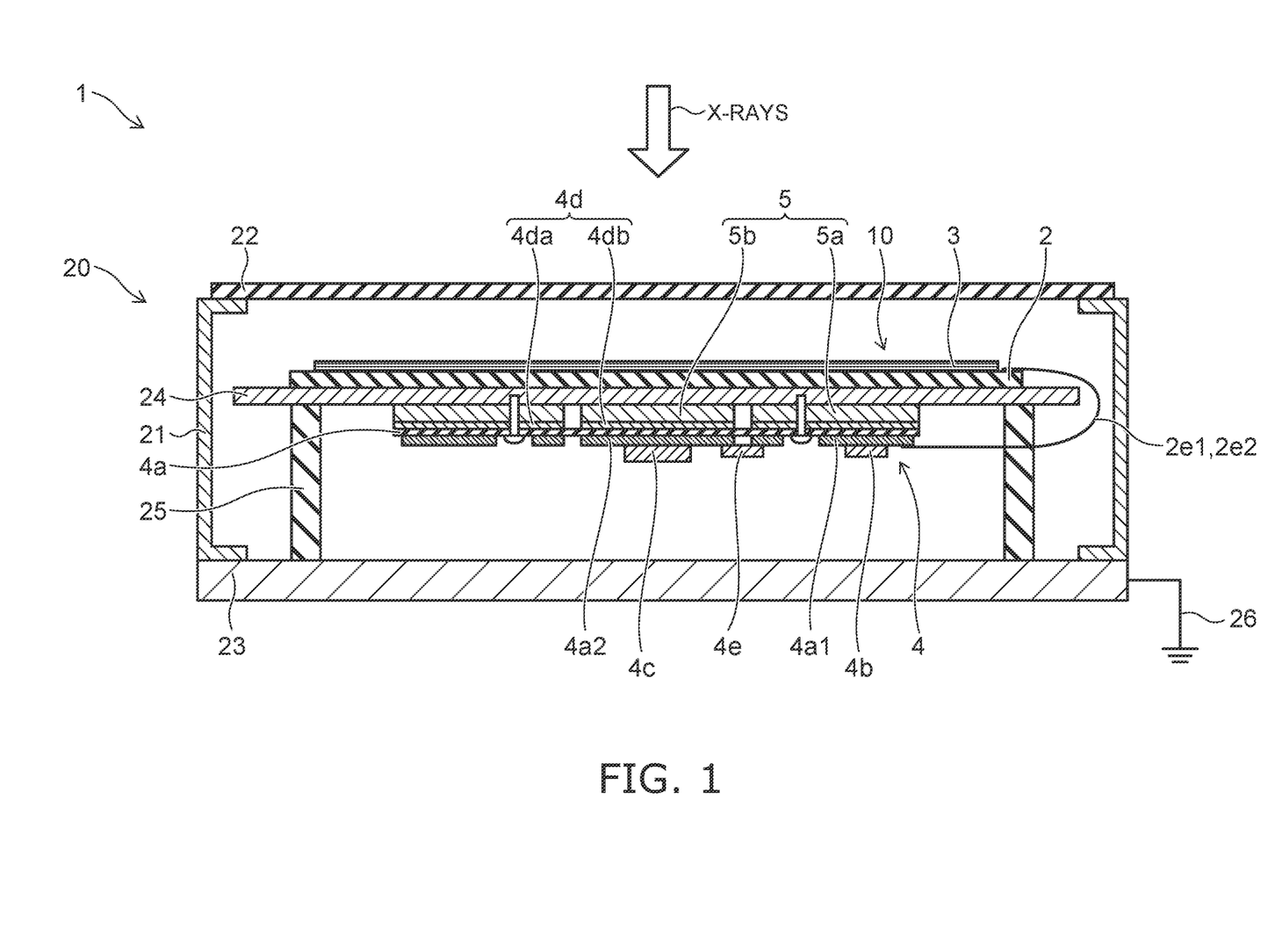
FIG. 1 is a schematic cross-sectional view illustrating an X-ray detector according to the embodiment.

FIG. 1 is a schematic cross-sectional view illustrating the X-ray detector 1 according to the embodiment.

Figure 2:
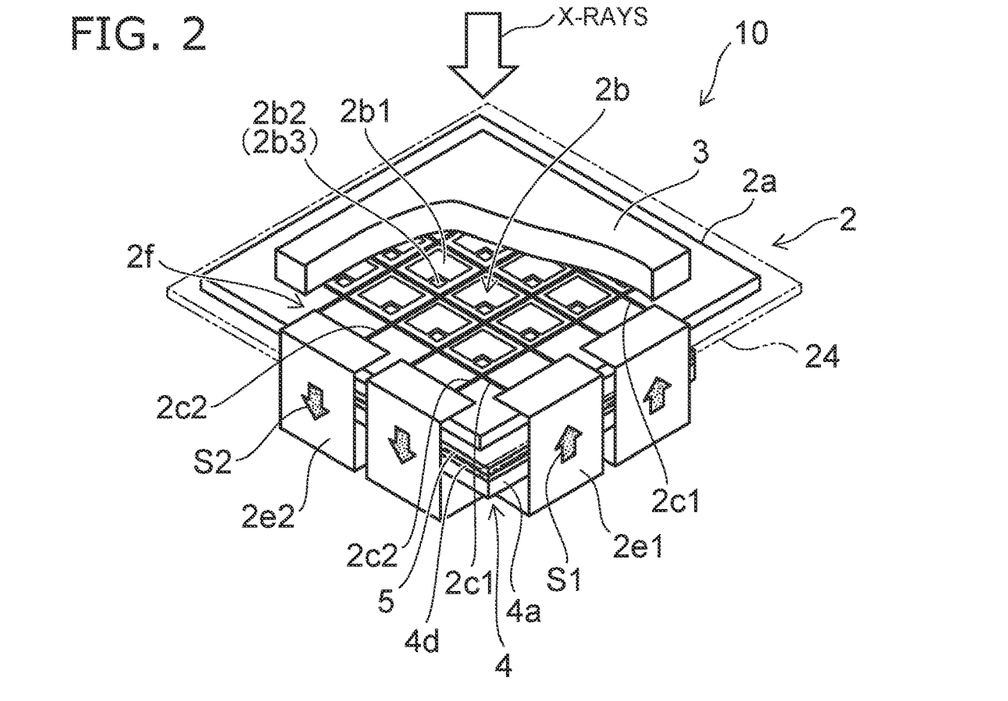
FIG. 2 is a schematic perspective view illustrating a detection module.

FIG. 2 is a schematic perspective view illustrating a detection module 10.

Figure 3:
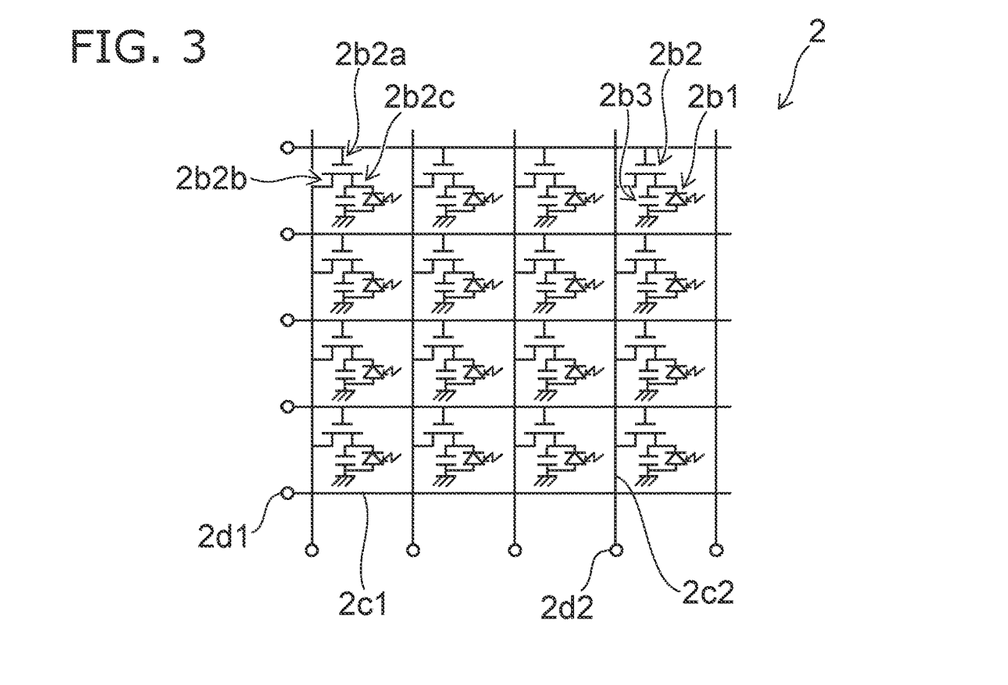
FIG. 3 is a circuit diagram of an array substrate.

FIG. 3 is a circuit diagram of an array substrate 2.

Figure 4:
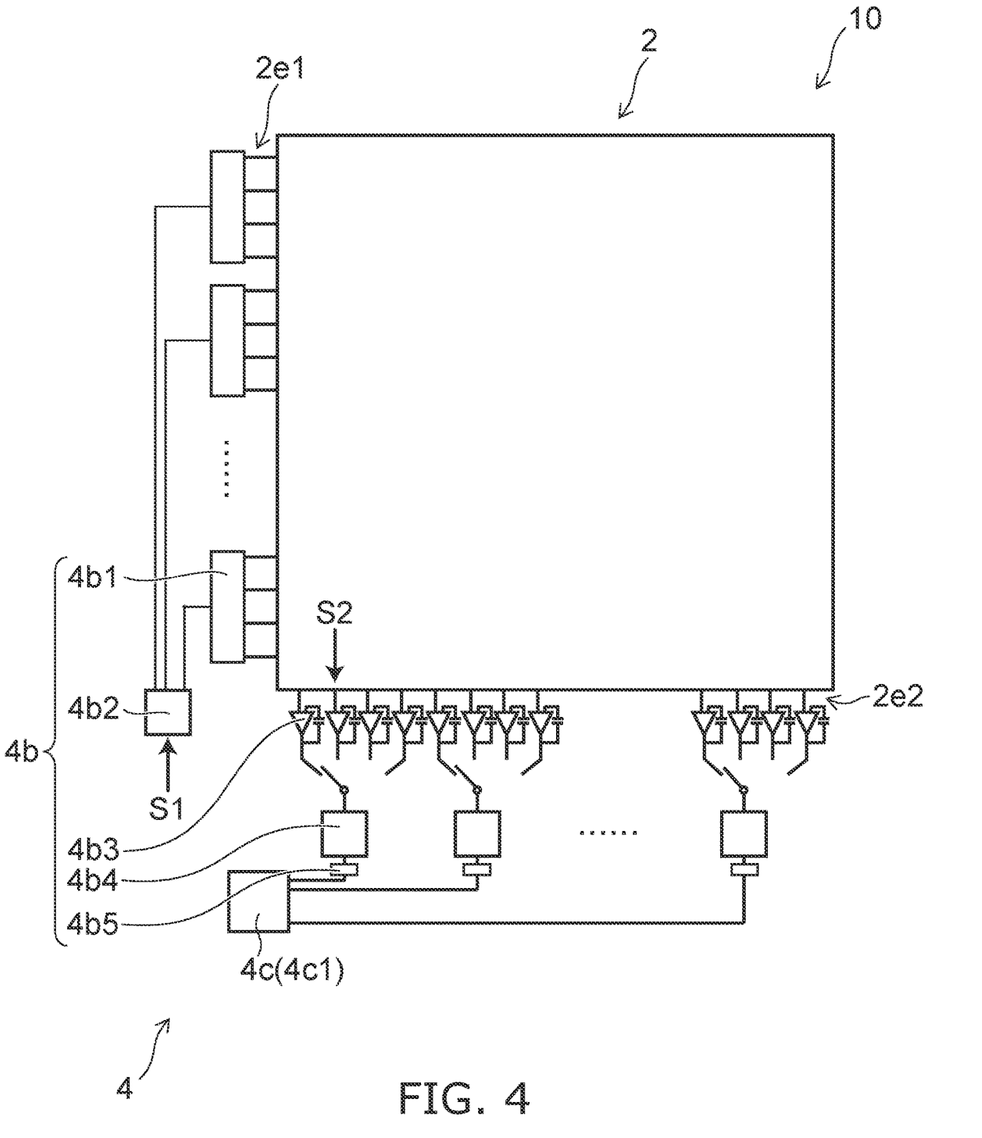
FIG. 4 is a block diagram of the detection module.

FIG. 4 is a block diagram of the detection module 10.

As shown in FIGS. 1 to 4, the X-ray detector 1 can include the detection module 10 and a housing 20.

The detection module 10 can include the array substrate 2, a scintillator 3, a circuit board 4, and a conductive part 5.

The detection module 10 can be located inside the housing 20.

The array substrate 2 uses the scintillator 3 to convert the fluorescence converted from the X-rays into a charge. As shown in FIG. 1, for example, the array substrate 2 can be located at the surface of a support plate 24 at the side of incidence of the X-rays.

The array substrate 2 can include a substrate $2a$, a photoelectric conversion part $2b$, a control line (or gate line) $2c1$, a data line (or signal line) $2c2$, a protective layer $2f$, etc. The numbers of the photoelectric conversion parts $2b$, control lines $2c1$, data lines $2c2$, etc., are not limited to those illustrated.

In the X-ray detector 1 according to the embodiment, the photoelectric conversion part $2b$ is a detecting part that detects X-rays in collaboration with the scintillator 3.

The substrate $2a$ is plate-shaped and can be formed from, for example, alkali-free glass, a polyimide resin, etc. For example, the planar shape of the substrate $2a$ can be quadrilateral.

Multiple photoelectric conversion parts $2b$ can be located at the surface of the substrate $2a$ at the side opposite to the support plate 24 side. The photoelectric conversion parts $2b$ can be located in regions defined by the control lines $2c1$ and the data lines $2c2$. The multiple photoelectric conversion parts $2b$ can be provided to be arranged in a matrix configuration. One photoelectric conversion part $2b$ corresponds to one pixel (pixel) of an X-ray image.

A photoelectric conversion element $2b1$ and a thin film transistor (TFT; Thin Film Transistor) $2b2$, i.e., a switching element, can be located in each of the multiple photoelectric conversion parts $2b$.

Also, a storage capacitor $2b3$ that stores the converted charge can be provided in the photoelectric conversion element $2b1$. For example, the storage capacitor $2b3$ can be film-shaped and can be located under each thin film transistor $2b2$. However, according to the capacitance of the photoelectric conversion element $2b1$, the photoelectric conversion element $2b1$ can also be used as the storage capacitor $2b3$.

For example, the photoelectric conversion element $2b1$ can be a photodiode, etc.

The thin film transistor $2b2$ can switch between storing and discharging charge to and from the storage capacitor $2b3$. As shown in FIG. 3, the thin film transistor $2b2$ can include a gate electrode $2b2a$, a drain electrode $2b2b$, and a source electrode $2b2c$. The gate electrode $2b2a$ of the thin film transistor $2b2$ can be electrically connected with the corresponding control line $2c1$. The drain electrode $2b2b$ of the thin film transistor $2b2$ can be electrically connected with the corresponding data line $2c2$. The source electrode $2b2c$ of the thin film transistor $2b2$ can be electrically connected to the corresponding photoelectric conversion element $2b1$ and storage capacitor $2b3$. Also, the storage capacitor $2b3$ and the anode side of the photoelectric conversion element $2b1$ can be electrically connected to a ground (an analog ground) of a wiring pattern $4a1$ to which an analog circuit $4b$ described below is electrically connected.

Multiple control lines $2c1$ can be provided to be parallel to each other at a prescribed spacing. For example, the control line $2c1$ can extend in a row direction. One control line $2c1$ can be electrically connected with one of multiple wiring pads $2d1$ located at the peripheral edge vicinity of the substrate $2a$. One of the multiple interconnects located in a flexible printed circuit board $2e1$ can be electrically connected to one wiring pad $2d1$.

The other ends of the multiple interconnects located in the flexible printed circuit board $2e1$ each can be electrically connected with the analog circuit $4b$ (a gate driver $4b1$) located in the circuit board 4.

Multiple data lines $2c2$ can be provided to be parallel to each other at a prescribed spacing. For example, the data line $2c2$ can extend in a column direction orthogonal to the row direction. One data line $2c2$ can be electrically connected with one of multiple wiring pads $2d2$ located at the peripheral edge vicinity of the substrate $2a$. One of the multiple interconnects located in a flexible printed circuit board $2e2$ can be electrically connected to one wiring pad $2d2$. The other ends of the multiple interconnects located in the flexible printed circuit board $2e2$ each can be electrically connected with the analog circuit $4b$ (an integrating amplifier $4b3$) located in the circuit board 4.

For example, the control line $2c1$ and the data line $2c2$ can be formed using a low-resistance metal such as aluminum, chrome, etc.

The protective layer $2f$ can cover the photoelectric conversion part $2b$, the control line $2c1$, the data line $2c2$, etc. The protective layer $2f$ can include, for example, at least one of an oxide insulating material, a nitride insulating material, an oxynitride insulating material, or a resin.

As shown in FIG. 2, the scintillator 3 can be located on the multiple photoelectric conversion parts $2b$. The scintillator 3 can convert the incident X-rays into fluorescence. The scintillator 3 can be provided to cover the region (the effective pixel region) on the substrate $2a$ in which the multiple photoelectric conversion parts $2b$ are located.

For example, the scintillator 3 can be formed using cesium iodide (CsI):thallium (Tl), sodium iodide (NaI):thallium (Tl), cesium bromide (CsBr):europium (Eu), etc. The scintillator 3 can be formed using vacuum vapor deposition. If the scintillator 3 is formed using vacuum vapor deposition, a scintillator 3 that is made of an aggregate of multiple columnar crystals can be formed.

Also, for example, the scintillator 3 can be formed using terbium-activated sulfated gadolinium ($Gd_2O_2S/Tb$ or GOS), etc. In such a case, a trench part having a matrix configuration can be formed so that a quadrilateral prism-shaped scintillator 3 is provided for each of the multiple photoelectric conversion parts $2b$.

Also, a reflective layer that covers the front side of the scintillator 3 (the incident surface side of the X-ray) can be provided in the detecting part 10 to increase the utilization efficiency of the fluorescence and improve the sensitivity characteristics.

Also, a moisture-resistant part that covers the scintillator 3 and the reflective layer can be provided to suppress degradation of the characteristics of the scintillator 3 and the characteristics of the reflective layer due to water vapor included in the air.

For example, the circuit board 4 can be located, with the conductive part 5 interposed, at the surface of the support plate 24 at the side opposite to the side of the incidence of the X-rays. For example, the circuit board 4 can be mounted to the support plate 24 by using a fastening member such as a screw, etc. The circuit board 4 can be electrically connected with the array substrate 2 via the flexible printed circuit boards $2e1$ and $2e2$.

The circuit board 4 can include a substrate $4a$, the analog circuit $4b$, a digital circuit $4c$, a ground $4d$, and an inductor $4e$.

The substrate $4a$ is plate-shaped and can include the wiring patterns $4a1$ and $4a2$ at the surface at the side opposite to the conductive part 5 side.

As described below, the analog circuit 4b can include the multiple gate drivers 4b1, a row selection circuit 4b2, the multiple integrating amplifiers 4b3, multiple selection circuits 4b4, and multiple AD converters 4b5. In such a case, the components and/or circuits that are included in the analog circuit 4b can be housed as an integrated circuit in one package. The package in which the analog circuit 4b is housed can be electrically connected with the wiring pattern 4a1. The wiring pattern 4a1 can be electrically connected with the flexible printed circuit boards 2e1 and 2e2. In other words, the analog circuit 4b can be electrically connected with the multiple control lines 2c1 via the flexible printed circuit board 2e1. The analog circuit 4b can be electrically connected with the multiple data lines 2c2 via the flexible printed circuit board 2e2.

As described below, the digital circuit 4c can include an image processing circuit 4c1. In such a case, the components and/or circuits that are included in the digital circuit 4c can be housed as an integrated circuit in one package. The package in which the digital circuit 4c is housed can be electrically connected with a wiring pattern 4a2. The package in which the digital circuit 4c is housed can be located in a region of the wiring pattern 4a2 in which a ground (a digital ground) is located.

The analog circuit 4b can read an image data signal S2 from the multiple photoelectric conversion parts 2b. Also, the analog circuit 4b may convert the image data signal S2 that is read into a digital signal.

As shown in FIG. 4, the analog circuit 4b can include the multiple gate drivers 4b1, the row selection circuit 4b2, the multiple integrating amplifiers 4b3, the multiple selection circuits 4b4, and the multiple AD converters 4b5. It is sufficient for the multiple AD converters 4b5 to be provided in one of the analog circuit 4b or the digital circuit 4c. A case where the multiple AD converters 4b5 are provided in the analog circuit 4b will now be described as an example.

A control signal S1 can be input to the row selection circuit 4b2. For example, the control signal S1 can be input from the image processing circuit 4c1, etc., to the row selection circuit 4b2. The row selection circuit 4b2 can input the control signal S1 to the corresponding gate driver 4b1 according to the scanning direction of the X-ray image. The gate driver 4b1 can input the control signal S1 to the corresponding control lines 2c1.

For example, the gate drivers 4b1 can sequentially input the control signal S1 to the control lines 2c1 via the flexible printed circuit boards 2e1. The thin film transistors 2b2 are set to the on-state by the control signal S1 input to the control lines 2c1; and the charge (the image data signal S2) from the storage capacitors 2b3 can be received.

Also, one integrating amplifier 4b3 can be electrically connected with one data line 2c2. The integrating amplifiers 4b3 can sequentially receive the image data signal S2 from the photoelectric conversion parts 2b. Then, the integrating amplifier 4b3 can integrate the current flowing within a certain amount of time and output a voltage corresponding to the integral to the selection circuit 4b4. Thus, the value of the current (the charge amount) flowing through the data line 2c2 within a prescribed interval can be converted into a voltage value. In other words, the integrating amplifiers 4b3 can convert the image data information corresponding to the intensity distribution of the fluorescence generated in the scintillator 3 into potential information.

The selection circuit 4b4 can sequentially read the image data signal S2 converted into the potential information by selecting the integrating amplifier 4b3 to be read.

The AD converter 4b5 can sequentially convert the image data signal S2 that is read into a digital signal. The image data signal S2 that is converted into the digital signal can be input to the digital circuit 4c (the image processing circuit 4c1).

The digital circuit 4c can include the image processing circuit 4c1. The image processing circuit 4c1 can configure an X-ray image based on the signals from the analog circuit 4b.

The data of the configured X-ray image can be output from the digital circuit 4c to an external device.

When the multiple AD converters 4b5 are provided in the analog circuit 4b, the image processing circuit 4c1 can configure the X-ray image based on the digital signal from the analog circuit 4b. When the multiple AD converters 4b5 are provided in the digital circuit 4c, the digital circuit 4c can convert the image data signal S2 (the analog signal) from the analog circuit 4b into a digital signal and configure the X-ray image based on the converted digital signal.

The ground 4d can be located at the surface of the substrate 4a at the conductive part 5 side. Also, the ground 4d can be located in the entire region of the surface of the substrate 4a at the conductive part 5 side, or can be located in a partial region of the surface at the conductive part 5 side of the substrate 4a. For example, there are cases where the elements included in the analog circuit 4b and/or the digital circuit 4c are located also at the surface of the substrate 4a at the conductive part 5 side. In such a case, the ground 4d can be located in a region of the substrate 4a in which the elements included in the analog circuit 4b and/or the digital circuit 4c are not located.

For example, the ground 4d can be film-shaped and can be formed from a conductive material such as copper, etc. Also, the ground 4d can be subdivided into a part 4da that is electrically connected with the ground (the analog ground) of the wiring pattern 4a1 to which the analog circuit 4b is electrically connected, and a part 4db that is electrically connected with the ground (the digital ground) of the wiring pattern 4a2 to which the digital circuit 4c is electrically connected. The electrical connection between the ground of the wiring pattern 4a1 and the part 4da of the ground 4d can be performed by multiple conduction vias extending through the substrate 4a in the thickness direction. The electrical connection between the ground of the wiring pattern 4a2 and the part 4db of the ground 4d can be performed by multiple conduction vias extending through the substrate 4a in the thickness direction.

As shown in FIG. 1, the inductor 4e can be electrically connected between the analog ground and the digital ground.

Here, as described above, the analog circuit 4b reads the image data signal S2 from the array substrate 2. The digital circuit 4c configures the X-ray image based on the signal from the analog circuit 4b. The analog circuit 4b and the digital circuit 4c each include ground lines that are separated into an analog ground and a digital ground.

There are many cases where a signal including much noise flows in the digital ground. For example, there are cases where a signal that includes much noise from a power supply for driving the image processing circuit 4c1, etc., flows in the digital ground. Also, the analog ground is electrically connected to the housing 20, etc., to stabilize the potential of the analog ground. Therefore, the noise of the digital ground side easily mixes into the analog ground side via a cover 21, a base 23, a spacer 25, the support plate 24, the conductive part 5, etc. When mixing into the analog ground side, there is a risk that the noise of the digital ground side may become noise of the X-ray image and degrade the quality of the X-ray image.

Therefore, the inductor 4e electrically connects between the analog ground and the digital ground. The inductor 4e includes, for example, a main body formed from a ceramic or a magnetic substance such as ferrite or the like, and a conductive body that is located inside the main body and is conductive.

Therefore, when noise flows through the conductive body, at least a portion of the noise can be converted into heat. As a result, the noise of the digital ground side can be prevented from mixing into the image data signal S2 read from the array substrate 2 (the multiple photoelectric conversion parts 2b) via the digital ground and the analog ground.

Here, to perform an accurate diagnosis when the X-ray detector 1 is used in general medical care, etc., it is desirable for the X-ray detector 1 to have higher density by providing more photoelectric conversion parts 2b and to have faster reading and processing of the image data signal S2. Therefore, faster processing in the digital circuit 4c is necessary, and there is a tendency for the operating clock to be faster and for noise having many high-frequency components to increase.

If the inductor 4e is provided, high-frequency potential fluctuation (the high-frequency components of noise) can be effectively removed. Therefore, even when the operating clock is faster, the noise can be prevented from mixing into the image data signal S2 read from the array substrate 2 (the multiple photoelectric conversion parts 2b).

Also, even if the noise of the digital ground side flows in the conductive part 5, the path of the noise is a short loop between the conductive part 5 and the substrate 4a. Therefore, the noise can be prevented from mixing into other circuits, etc., and becoming noise of the X-ray image.

The conductive part 5 can be located between the ground 4d and the support plate 24. The conductive part 5 is conductive and can electrically connect the ground 4d and the support plate 24. When the ground 4d is subdivided into the part 4da and the part 4db, the conductive part 5 can also be subdivided into a part 5a that is located between the support plate 24 and the part 4da of the ground 4d and a part 5b that is located between the support plate 24 and the part 4db of the ground 4d.

Although a case where the circuit board 4 is located at the support plate 24 is illustrated as an example in FIG. 1, the circuit board 4 can be located, with the conductive part 5 interposed, at the base 23, the inner surface of the cover 21, etc., located in the housing 20. In other words, the conductive part 5 can be located inside the housing 20 between the film-shaped ground 4d located at the circuit board 4 and a conductive plate-shaped body located in the housing 20.

The conductive part 5 is conductive and can be formed from a softer material than the material of the ground 4d. For example, the conductive part 5 can include nickel, a nickel alloy, tin, a tin alloy etc. Also, the conductive part 5 may be, for example, a resin, rubber, or the like that includes particles and/or fibers formed from a conductive material such as a metal, etc.

In other words, the conductive part 5 may include an organic material that is conductive. However, considering impedance reduction, it is favorable for the conductive part 5 to include a metal such as nickel, etc.

Figure 5:
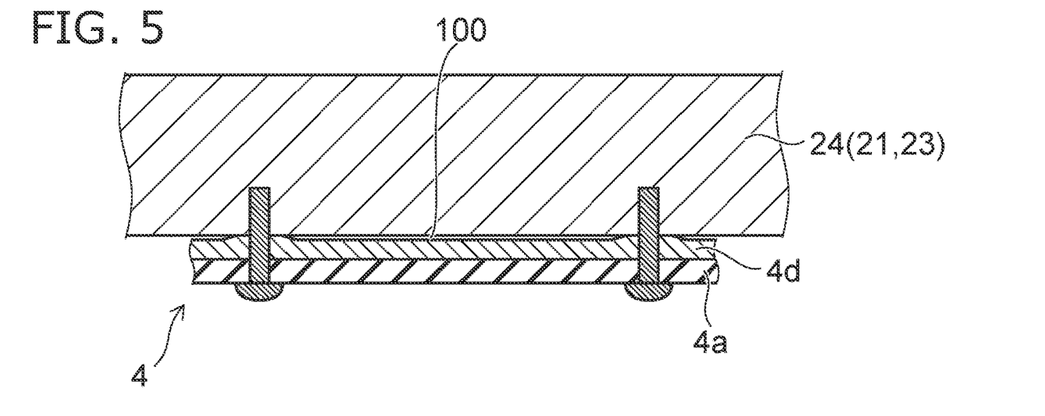
FIG. 5 is a schematic cross-sectional view illustrating a connection between a support plate and a circuit board according to a comparative example.

FIG. 5 is a schematic cross-sectional view illustrating a connection between the circuit board 4 and the support plate 24 according to a comparative example.

As shown in FIG. 5, the ground 4d is located at the surface of the substrate 4a at the support plate 24 side. Generally, the ground 4d is formed by forming a film of a metal such as copper, etc., on the surface of the substrate 4a by plating, etc.

Therefore, there are many cases where an unevenness is formed in the surface of the ground 4d at the side opposite to the substrate 4a side. Also, when there is unevenness or waviness in the surface of the substrate 4a, there are cases where the unevenness or waviness of the surface of the substrate 4a is transferred to the surface of the ground 4d. Also, there are cases where there is unevenness or waviness in the surface of the support plate 24 as well.

Therefore, there are cases where a gap 100 occurs between the ground 4d and the support plate 24 when the substrate 4a on which the ground 4d is located is mounted to the support plate 24 by using a fastening member such as a screw, etc. For example, as shown in FIG. 5, there are cases where the ground 4d and the support plate 24 contact each other at the position at which the fastening member is located, but the gap 100 occurs between the ground 4d and the support plate 24 between the fastening member and the fastening member, etc. When the gap 100 occurs between the ground 4d and the support plate 24, there is a risk that the impedance between the ground 4d and the support plate 24 may increase, and noise reduction may be difficult.

Figure 6:
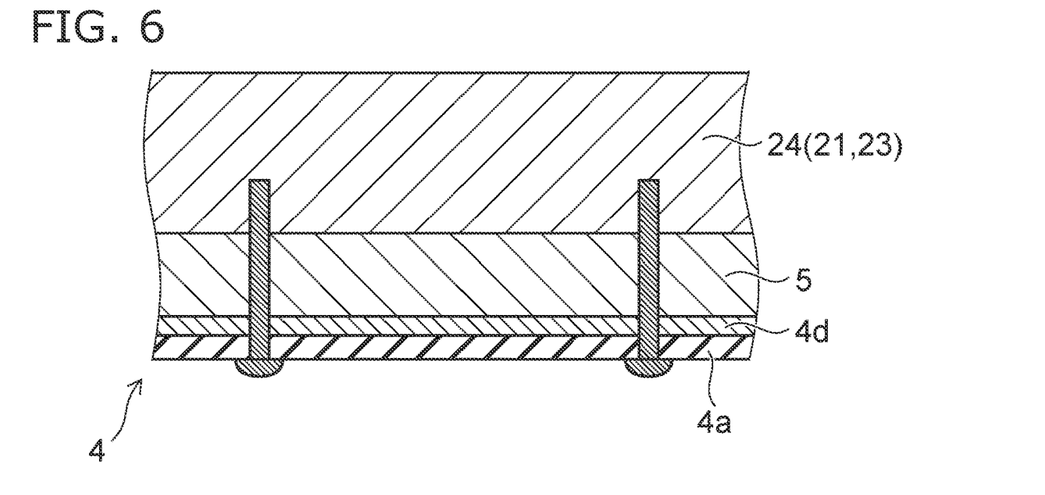
FIG. 6 is a schematic cross-sectional view illustrating a connection between a support plate and a circuit board according to the embodiment.

FIG. 6 is a schematic cross-sectional view illustrating the connection between the circuit board 4 and the support plate 24 according to the embodiment.

As shown in FIG. 6, the ground 4d is located at the surface of the substrate 4a at the support plate 24 side. The conductive part 5 is located between the ground 4d and the support plate 24. As described above, the conductive part 5 is conductive and is formed from a softer material than the material of the ground 4d. For example, the conductive part 5 is formed from nickel, a nickel alloy, tin, a tin alloy, a conductive organic material, etc. Therefore, the conductive part 5 and the ground 4d are closely adhered more easily even when there is an unevenness and waviness at the surface of the ground 4d at the side opposite to the substrate 4a side. The conductive part 5 and the support plate 24 are closely adhered more easily even when there is an unevenness and waviness in the surface of the support plate 24.

As a result, the noise can be reduced because the impedance between the ground 4d and the support plate 24 can be reduced. To reduce the impedance, it is favorable to form the conductive part 5 from a metal such as nickel, a nickel alloy, tin, a tin alloy etc., rather than forming the conductive part 5 from an organic material that is conductive.

Figure 7:
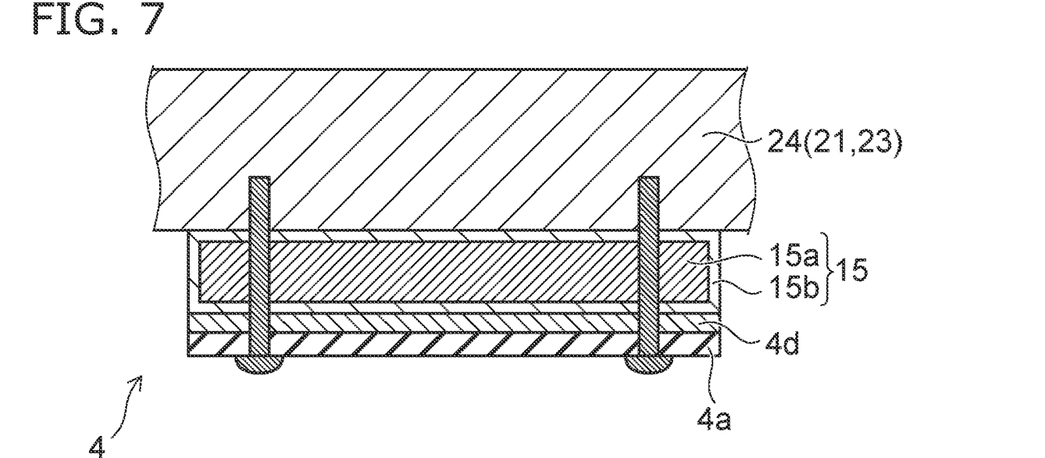
FIG. 7 is a schematic cross-sectional view illustrating a connection between a support plate and a circuit board according to another embodiment.

FIG. 7 is a schematic cross-sectional view illustrating a connection between the circuit board 4 and the support plate 24 according to another embodiment.

As shown in FIG. 7, the ground 4d is located at the surface of the substrate 4a at the support plate 24 side. A conductive part 15 is located between the ground 4d and the support plate 24. The conductive part 15 can include a main part 15a and a covering part 15b.

The main part 15a is plate-shaped and can be formed from a material that is conductive. For example, the main part 15a can be formed from a low-resistance metal such as copper, aluminum, etc.

The covering part 15b can be located at least at the surface of the main part 15a at the ground 4d side and the surface of the main part 15a at the support plate 24 side. As illustrated in FIG. 7, the covering part 15b can also be located over the entire surface of the main part 15a. The covering part 15b is film-shaped and can be formed from a material that is conductive. For example, the covering part 15b can be formed from a softer material than the material of the ground 4d. The covering part 15b can include, for example, nickel, a nickel alloy, tin, a tin alloy etc. For example, the covering part 15b can be formed by plating nickel, a nickel alloy, tin, a tin alloy etc., on the main part 15a.

Because the covering part 15b that includes a softer material than the material of the ground 4d is located at the surface of the conductive part 15, the conductive part 15 (the covering part 15b) and the ground 4d are closely adhered more easily even when there is an unevenness or waviness in the surface of the ground 4d at the side opposite to the substrate 4a side. The conductive part 15 (the covering part 15b) and the support plate 24 are closely adhered more easily even when there is an unevenness or waviness in the surface of the support plate 24.

As a result, the noise can be reduced because the impedance between the ground 4d and the support plate 24 can be reduced.

Returning now to FIG. 1, the housing 20 will be described.

As shown in FIG. 1, the housing 20 can include the cover 21, an incident window 22, the base 23, the support plate 24, the spacer 25, and an earth wire 26.

The cover 21 can be box-shaped and can have openings at the incident side of the X-rays and at the side opposite to the incident side of the X-rays. Considering weight reduction, for example, the cover 21 can be formed using a light metal such as an aluminum alloy, etc.

The incident window 22 is plate-shaped and can be provided to block the opening of the cover 21 at the incident side of the X-rays. The incident window 22 can transmit the X-rays. The incident window 22 can be formed of a material having a low X-ray absorptance. For example, the incident window 22 can be formed using a carbon-fiber-reinforced plastic, etc.

The base 23 is plate-shaped and can be provided to block the opening of the cover 21 at the side opposite to the incident side of the X-rays. The base 23 may be formed to have a continuous body with the cover 21. The material of the base 23 is not particularly limited as long as the material is somewhat rigid. For example, the material of the base 23 can be similar to the material of the cover 21. The ground 4d that is provided in the circuit board 4 (the substrate 4a) is electrically connected to the cover 21 and/or the base 23 via the conductive part 5 (15), the support plate 24, and the spacer 25. Therefore, considering noise reduction, it is favorable for the cover 21 and/or the base 23 to be formed using a material that is conductive (e.g., a metal such as an aluminum alloy, etc.).

The support plate 24 is plate-shaped and can be located inside the cover 21. The array substrate 2 can be located at the surface of the support plate 24 at the incident window 22 side. In such a case, the array substrate 2 may be fixed to the support plate 24; and the array substrate 2 may be detachable from the support plate 24. The circuit board 4 can be located, with the conductive part 5 (15) interposed, at the surface of the support plate 24 at the side opposite to the incident window 22 side. Also, as described above, the circuit board 4 can be located at the base 23, the inner surface of the cover 21, etc., with the conductive part 5 (15) interposed.

It is favorable for the material of the support plate 24 to be conductive and to have a somewhat high X-ray absorptance. The material of the support plate 24 can be, for example, a metal such as stainless steel, an aluminum alloy, etc.

The spacer 25 is columnar or tubular; and multiple spacers 25 can be located inside the cover 21. The multiple spacers 25 can be located between the support plate 24 and the base 23. For example, the fixation of the spacer 25 and the support plate 24 can be performed using a fastening member such as a screw, etc. The material of the spacer 25 is not particularly limited as long as the material is somewhat rigid and is conductive. For example, the spacer 25 can be formed using a metal, etc.

The configuration, arrangement position, number, material, and the like of the spacer 25 are not limited to those illustrated. Also, the spacer 25 may not be used if the support plate 24 is supported inside the cover 21. For example, a rib that protrudes into the cover 21 from the inner surface of the cover 21 may be provided, and the support plate 24 may be supported by the rib.

For example, one end of the earth wire 26 can be electrically connected with at least one of the cover 21 or the base 23. The other end of the earth wire 26 can be grounded. If the earth wire 26 is provided, the ground 4d that is provided in the circuit board 4 can be grounded via the conductive part 5 and the housing 20. Therefore, the noise reduction described above can be effectively performed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions. Moreover, above-mentioned embodiments can be combined mutually and can be carried out.

What is claimed is:

1. A radiation detector, comprising:
    a housing;
    an array substrate located inside the housing, the array substrate including a plurality of detecting parts detecting radiation directly or in collaboration with a scintillator;
    a circuit board located inside the housing, the circuit board being electrically connected with the array substrate; and
    a conductive part located between a ground and a plate-shaped body inside the housing, the ground being film-shaped and being located in the circuit board, the plate-shaped body being conductive and being located in the housing,
    the conductive part being conductive and including a softer material than a material of the ground.

2. The radiation detector according to claim 1, wherein the conductive part includes:
    a main part that is plate-shaped and conductive; and
    a covering part that is film-shaped and is located on at least a surface of the main part at the ground side and a surface of the main part at the plate-shaped body side, and
    the covering part is conductive and includes a softer material than the material of the ground.

3. The radiation detector according to claim 1, wherein the ground includes copper, and
    the conductive part includes one of nickel, a nickel alloy, tin, a tin alloy, or a conductive organic material.

4. The radiation detector according to claim 2, wherein
the ground includes copper,
the main part includes copper, and
the covering part includes one of nickel, a nickel alloy, tin, or a tin alloy.

5. The radiation detector according to claim 1, wherein
the plate-shaped body is located inside the housing,
the array substrate is located at a surface of the plate-shaped body at a side of incidence of the radiation, and
the circuit board is located, with the conductive part interposed, at a surface of the plate-shaped body at a side opposite to the side of incidence of the radiation.

6. The radiation detector according to claim 1, wherein
the circuit board is mounted to the plate-shaped body by using a fastening member.

7. The radiation detector according to claim 1, wherein
the circuit board is electrically connected with the array substrate via a flexible printed circuit board.

8. The radiation detector according to claim 1, wherein
the circuit board includes a substrate,
an analog circuit, a digital circuit, and an inductor are located at a surface of the substrate at a side opposite to the conductive part side, and
the ground is located at a surface of the substrate at the conductive part side.

9. The radiation detector according to claim 8, wherein
the analog circuit includes a plurality of gate drivers, a row selection circuit, an integrating amplifier, and a selection circuit.

10. The radiation detector according to claim 9, wherein
the analog circuit reads an image data signal from the plurality of detecting parts.

11. The radiation detector according to claim 9, wherein
the analog circuit further includes an AD converter.

12. The radiation detector according to claim 11, wherein
the analog circuit reads an image data signal from the plurality of detecting parts and converts the image data signal that is read into a digital signal.

13. The radiation detector according to claim 8, wherein
the digital circuit includes an image processing circuit.

14. The radiation detector according to claim 13, wherein
the analog circuit reads an image data signal from the plurality of detecting parts, and
the image processing circuit converts the image data signal that is read into a digital signal and configures a radiation image based on the converted digital signal.

15. The radiation detector according to claim 13, wherein
the analog circuit reads an image data signal from the plurality of detecting parts and converts the image data signal that is read into a digital signal, and
the image processing circuit configures a radiation image based on the converted digital signal.

16. The radiation detector according to claim 8, wherein
the ground is located in an entire region of the surface of the substrate at the conductive part side.

17. The radiation detector according to claim 8, wherein
the ground is located in a partial region of the surface of the substrate at the conductive part side.

18. The radiation detector according to claim 8, wherein
the ground includes:
a first ground to which a ground line of the analog circuit is electrically connected; and
a second ground to which a ground line of the digital circuit is electrically connected.

19. The radiation detector according to claim 18, wherein
the inductor electrically connects the first ground and the second ground.

20. The radiation detector according to claim 19, wherein
the inductor converts at least a portion of noise flowing from the second ground to the first ground into heat.

\* \* \* \* \*